United States Patent
Davis et al.

(10) Patent No.: US 6,915,912 B2
(45) Date of Patent: *Jul. 12, 2005

(54) COUPLING DEVICE FOR COUPLING INSTRUMENT ORGANIZERS WITH MOVABLE STABILIZING POSTS TOGETHER

(75) Inventors: Phillip Davis, Weston, CT (US); Vito L. DiPinto, South Windsor, CT (US)

(73) Assignee: General Hospital Supply Corporation, Wilton, CT (US)

( * ) Notice: Subject to any disclaimer, the term of this patent is extended or adjusted under 35 U.S.C. 154(b) by 120 days.

This patent is subject to a terminal disclaimer.

(21) Appl. No.: 09/843,211

(22) Filed: Apr. 25, 2001

(65) Prior Publication Data

US 2001/0035384 A1 Nov. 1, 2001

Related U.S. Application Data

(63) Continuation-in-part of application No. 09/515,284, filed on Feb. 29, 2000, now Pat. No. 6,367,637.

(51) Int. Cl.[7] .................................................. A47F 7/00
(52) U.S. Cl. ................... 211/85.13; 211/70.6; 211/184; 211/13.1
(58) Field of Search ............................... 211/85.13, 43, 211/70.6, 184, 13.1; 206/370

(56) References Cited

U.S. PATENT DOCUMENTS

| | | | |
|---|---|---|---|
| 2,882,660 A | * | 4/1959 | Denton ...................... 53/139.6 |
| 3,258,293 A | * | 6/1966 | Sharp .......................... 297/483 |
| 3,736,935 A | | 6/1973 | Reimels |
| 4,040,884 A | | 8/1977 | Roth |
| 4,098,728 A | | 7/1978 | Rosenblatt |
| 4,229,420 A | | 10/1980 | Smith et al. |
| 4,342,391 A | | 8/1982 | Schainholz |
| 4,512,466 A | | 4/1985 | Delang |
| 4,641,749 A | | 2/1987 | Link et al. |
| 4,865,821 A | | 9/1989 | Langdon |
| 5,046,624 A | | 9/1991 | Murphy et al. |
| 5,072,835 A | | 12/1991 | Price et al. |
| 5,145,655 A | | 9/1992 | Darlak |
| 5,201,430 A | | 4/1993 | Artzer |
| 5,657,702 A | | 8/1997 | Ribeyrolles |
| 5,664,691 A | | 9/1997 | Boivin-Paradis |
| 5,904,703 A | | 5/1999 | Gilson |
| 5,944,729 A | | 8/1999 | Blake |
| 6,048,503 A | | 4/2000 | Riley et al. |
| 6,168,570 B1 | | 1/2001 | Ferrera |

OTHER PUBLICATIONS

Medical Action Industries, Inc. Product Literature (3 pages) Regarding Ancillary Products, No Date.
Contour Fabricators of Florida, Inc. Product Literature (2 pages) Re: Disposable Medical Surgical Prod. No Date.
Graphic Controls Corporation Product Brochure, (8 Pages) Copyright 1998.
DC Medical, Division of PSC Corporation Product Literature (single page), No Date.

* cited by examiner

Primary Examiner—Gregory J. Strimbu
(74) Attorney, Agent, or Firm—St. Onge Steward Johnston & Reens LLC

(57) ABSTRACT

An instrument organizer for at least partially supporting one or more surgical instruments includes a base structure having opposed terminal ends and at least one end post fixedly positioned at one terminal end of the base structure. The instrument organizer also includes at least one movable stabilizing structure that is mountable on the base structure at a location spaced from the end post, to thereby stabilize and at least partially support the one or more instruments. At least one of the base structure and the movable stabilizing structure may include a radiopaque material. Also, the end post may include a generally triangular shape in cross section and a coupling device for coupling multiple instrument organizers together. Further, a method of applying a radiopaque substance to the instrument organizer.

15 Claims, 4 Drawing Sheets

COUPLING DEVICE FOR COUPLING INSTRUMENT ORGANIZERS WITH MOVABLE STABILIZING POSTS TOGETHER

CROSS REFERENCE TO RELATED APPLICATION

This application is a continuation-in-part application of U.S. patent application Ser. No. 09/515,284, entitled "Instrument Organizer With Movable Stabilizing Post", filed Feb. 29, 2000 now U.S. Pat. No. 6,367,637 and assigned to the present assignee hereof.

BACKGROUND OF THE INVENTION

1. Field of the Invention

The present invention relates generally to organizers for organizing instruments and, more particularly, the present invention relates to organizers including a stabilizing post for separating and securing surgical instruments, e.g., before and during surgery, and in preparation for sterilization.

2. Related Art

Surgical instruments, such as hemostats, scissors, forceps, etc., are normally separated and organized during surgical procedures and also before sterilization by being laid on their side in a vertical or upright position on rolled-up cotton towels. The rolled-up cotton towels, which may have their outside edges taped, support the instruments such that the instruments can be more easily counted, selected and handled by a doctor or nurse during a surgical procedure, or while the instruments are assembled prior to sterilization.

Foam organizers have also been provided to support and group surgical instruments before and during actual use of the instruments. Such organizers can have an elongated base with fixed posts extending upwardly from ends of the base. The foam organizers support the instruments, with the instruments resting on the base and leaning against the posts, such that the instruments can be more easily counted, selected and handled by a doctor or nurse during a surgical procedure, or while the instruments are assembled prior to sterilization.

Such rolled cotton towels or foam organizers, with the surgical instruments supported thereon, are usually laid out on a tray or a table. Sometimes, however, before and during use of the surgical instruments, the instruments supported on the rolled towel or the organizer can topple over from their upright positions and become mixed and disorganized and, accordingly, more difficult to count, select and handle prior to actual use of the instruments, or while the instruments are assembled prior to sterilization. In addition, it is not uncommon for the cotton towels to produce lint, which can transmit microorganisms and result in contamination of the surgical instruments.

Accordingly, it is an object of the present invention to provide means for retaining surgical instruments in an organized and/or upright position.

It is another object to provide an instrument organizer, wherein, instruments supported thereon are less likely to topple over from an upright position prior to actual use or sterilization of the instruments and are, therefore, easier to count, select and handle.

It is a further object to provide an instrument organizer that is securable on a surface, such as on a tray or a table top, so that the organizer will not move while supporting instruments.

It is another object to provide an instrument organizer that is lint-free.

It is still another object to provide an instrument organizer that is detectable through radiographic techniques or the like.

It is a further object to provide an instrument organizer that reduces the required set up time such as the time associated with rolling up numerous towels.

It is still a further object to provide a couple for coupling multiple instrument organizers together in order to increase the space available for instruments and to insure that a particular order of the instruments and/or instrument organizers is retained.

As used herein, the term "self-gripping legs" refers to legs that, by themselves, grip and maintain a hold on a base sufficient to support implements such as surgical instruments in an upright manner.

SUMMARY OF THE INVENTION

An instrument organizer that overcomes the above-discussed disadvantages of the prior art, and which at least partially supports surgical instruments, comprises an elongated base that has a uniform, predetermined width. The base defines a continuous surface extending from a first side surface to an opposing second side surface thereof and includes two terminal ends. The instrument organizer may comprise at least one fixed end post that extends from a terminal end of the base and at least one movable stabilizing structure that includes two gripping legs extending from a central body. The gripping legs have opposing, inwardly facing surfaces spaced apart a distance substantially equal to the predetermined width of the base of the instrument organizer. The opposing, inwardly facing surfaces of the two gripping legs being dimensioned and configured to grip the first and second side surfaces of the base of the instrument organizer, respectively, so that the movable stabilizing structure can be attached to the base of the instrument organizer at any point between the terminal ends of the organizer and the central body is held in place by the gripping legs for retaining the surgical instruments in an organized and upright state at least partially on the organizer. In one particular embodiment of the present invention the at least one fixed end post comprises a generally triangular configuration in cross section. In another particular embodiment of the present invention, the continuous surface of the base comprises a contact portion having a non-linear shape in cross section.

In another embodiment of the present invention a couple for coupling a pair of instrument organizers is presented. The instrument organizers each may comprise an elongated base structure that includes a top surface and a front surface and a rear surface extending from the top surface and the front surface and the rear surface being disposed on opposing sides of the base structure. The elongated base structure may comprise a predetermined width as measured from the front surface to the rear surface and the elongated base structure may include opposed terminal ends. At least one first end post may be fixedly positioned at one terminal end of the base structure and at least one movable stabilizing structure may be provided that is mountable at any axially spaced location along a length of the base structure relative to the first end post. The movable stabilizing structure includes a body portion and opposed, spaced apart legs depending therefrom, the legs may be spaced apart a distance approximately equal to the predetermined width of the base structure to facilitate frictional engagement with the base structure to thereby stabilize and at least partially support one or more surgical instruments. The couple may comprise a coupling device for connecting at least one instrument organizer with another instrument organizer.

In a particular embodiment of the present invention, the coupling device comprises a wall portion that defines an aperture that is dimensioned and configured to receive adjoining end posts of each instrument organizer when the instrument organizers are disposed in juxtaposition.

In another embodiment of the present invention, an instrument organizer, for at least partially supporting one or more surgical instruments, includes a base structure having opposed terminal ends and at least one first end post fixedly positioned at one terminal end of the base structure. The instrument organizer also includes at least one movable stabilizing structure that is mountable on the base structure at a location spaced from the first end post, to thereby stabilize and at least partially support one or more instruments. At least one of the base structure and the movable stabilizing structure includes a radiopaque material.

In a particular embodiment of the present invention, the radiopaque material comprises at least one radiopaque string that, in turn, comprises at least one of a flexible polymer and a copolymer along with a radiopaque substance embedded therein. More particularly, the at least one of a flexible polymer and a copolymer may comprise polyvinyl chloride and the radiopaque substance may comprise a USP barium sulfate additive.

In a further particular embodiment, the radiopaque material may comprise at least one strand of material composed of a metallic substance. More specifically, the at least one strand may comprise multiple strands embedded within the base structure and/or in the movable stabilizing structure and the metallic substance may consist of at least one metal from the group consisting of platinum, gold and tungsten.

In a further embodiment, a method of applying a radiopaque material to an instrument organizer that comprises a base structure and a movable stabilizing structure is presented. The method comprises the steps of: providing a thermoplastic polymer; dispersing a sufficient quantity of radiopaque substance into the thermoplastic polymer to render the thermoplastic polymer identifiable on an X-ray image; and compressing the thermoplastic polymer into a polyurethane foam forming the base structure and/or the movable stabilizing structure.

Other features and advantages of the present invention will become apparent upon reading the following detailed description in conjunction with the accompanying drawings.

DETAILED DESCRIPTION OF THE INVENTION

Figure 1:
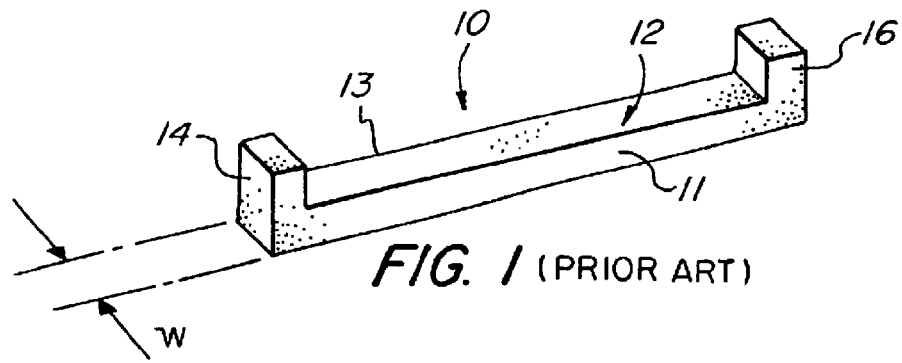
FIG. 1 is a perspective view of a prior art instrument organizer for supporting surgical instruments within a surgical tray.

Referring to FIG. 1, an existing surgical instrument organizer is shown generally at 10. The organizer is used for supporting and helping to organize surgical instruments, e.g., before and during actual use of the instruments and/or in preparation for sterilization of such instruments. The organizer 10 includes an elongated base 12 having front and rear surfaces 11, 13 spaced a uniform predetermined width "w" and fixed end posts 14, 16 extending upwardly from ends of the base.

Although not shown, surgical instruments, such as hemostats, scissors, forceps, etc., can be supported by the organizer 10 such that the instruments can be organized into separate groups and more easily selected and handled by a doctor or nurse during a surgical procedure and when assembling instruments prior to sterilization. The instrument organizer 10 replaces the rolled-up cotton towel described above.

Figure 2:
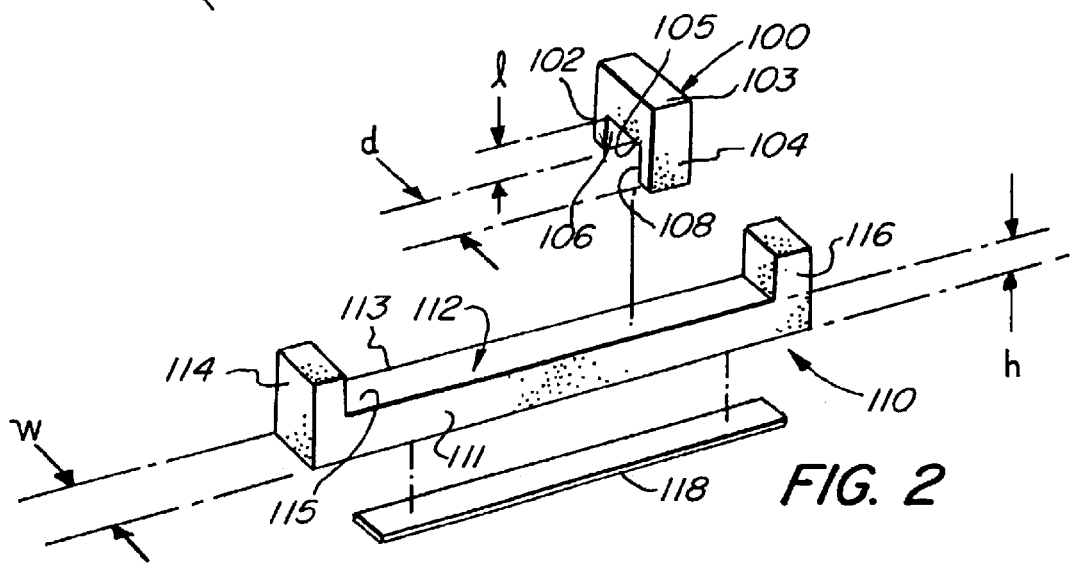
FIG. 2 is an exploded view, in perspective, of an instrument organizer, including a movable stabilizing post and a self-adhesive strip according to a first embodiment of the present invention.
Figure 3:
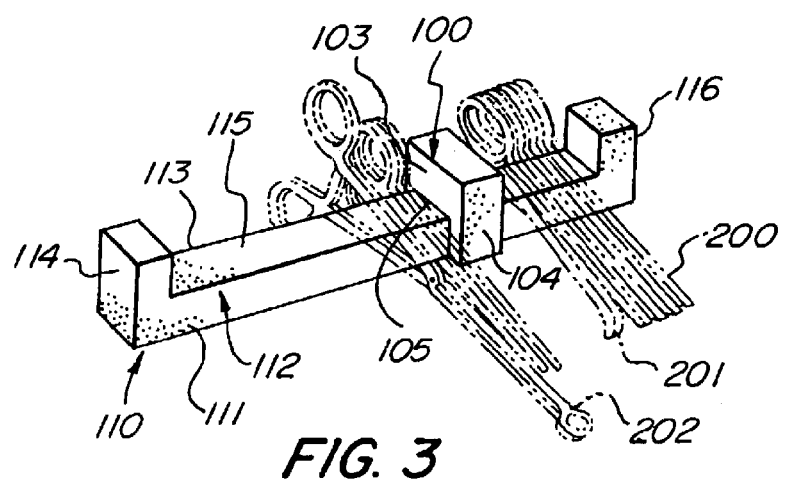
FIG. 3 is a perspective view of the instrument organizer of FIG. 2 disposed on a planar support and, in turn, supporting surgical instruments in an upright position, with the movable stabilizing post secured to the organizer and providing support to the instruments.

Referring to FIGS. 2 and 3, a movable stabilizing structure or post 100 according to one embodiment of the present invention is shown being used with an instrument organizer 110 similar to the instrument organizer 10 of FIG. 1. The movable stabilizing post 100 provides the benefit of maintaining instruments supported by the organizer in an organized and upright manner to ensure that the instruments can be more easily organized, counted, selected and handled by a doctor or nurse during a surgical procedure, or when assembling instruments prior to sterilization, and assures the operating team that the surgical instruments will be lint-free.

The movable stabilizing post 100 includes two gripping legs 102, 104 extending downwardly from a central body that defines a post 103, and having spaced apart, opposing, inwardly facing surfaces 106, 108. The opposing, inwardly facing surfaces 106, 108 of the gripping legs 102, 104 of the movable stabilizing post 100 are spaced apart a distance "d" substantially equal to the predetermined width "w" of the base 112 of the organizer 110.

The movable stabilizing post 100, therefore, is fit on the base 112 of the organizer 110 so that the opposing, inwardly facing surfaces 106, 108 of the gripping legs 102, 104 of the movable stabilizing post 100 may solely grip the front and rear surfaces 111, 113 of the base, whereby the movable stabilizing post can be attached to the base of the organizer at any point between the fixed end posts 114, 116 and be retained in place at that point by the gripping l gs. Preferably, a length "l" of the gripping legs 102, 104 is either not greater than or is equal to a height "h" of the base 112 of the organizer 110 so that a bottom surface 105 of the post 103 of the moveable stabilizing post 100 contacts a top surface 115 of the base 112 to provide additional stability. Preferably, as illustrated, the movable stabilizing post is formed from a blank of material such that the post 103 includes exterior surfaces which are generally planar and integral with corresponding exterior surfaces of the gripping legs 102, 104.

As shown in FIG. 3, the movable stabilizing post 100 can be positioned on the base 112 of the organizer 110 which is, in turn, disposed on a planar support surface 119. Use of the movable stabilizing post 100, insures that surgical instruments 200, 201, 202 will be maintained in an upright position between the movable stabilizing post and one of the fixed end posts 116 of the organizer. The movable stabilizing post 100 prevents instruments, partially supported on the organizer 110 and partially supported on planar support surface 119, from toppling over from their upright positions and becoming mixed and disorganized. The improved organization and accessibility provided by the organizer/stabilizing post find particular utility before and during a surgical procedure, and/or in preparation for sterilization.

Preferably, the organizer 110 and the movable stabilizing post 100 are both made of a non-woven, non-absorbent, lint-free material. The organizer 110 and the movable stabilizing post 100 are preferably made of a lint-free foam plastic which is, as illustrated and described below, insufficiently rigid to partially support surgical instruments 200, 201, 202 absent a planar support surface. In addition, it is envisioned that the organizer 110 and the movable stabilizing post 100 can be provided in a sterile state. Preferably the organizer 110 and the movable stabilizing post 100 are composed of a non-reticulated polyurethane foam having the physical properties provided in TABLE 1.

TABLE 1

| Physical Property (Tested According to ASTM D3574/86) | Minimum | Average |
| --- | --- | --- |
| Density | 2.0 ± 10% lbs./cu. ft. | 2.0 ± 10% lbs./cu. ft. |
| Tensile Strength | 22 psi. | 27 psi. |
| Ultimate Elongation | 58% | 85% |
| Tear Resistance | 1.1 ppi. | 1.6 ppi. |
| Compression set, $C_t$, % 50% Deflection | Max. 10% | Max. 10% |
| Compression Force Deflection, 70% Deflection | 2.4 psi. | 2.9 psi. |
| Indentation Force Deflection, lbs. 25% Deflection, 4 inches thick | 92 lbs. | 112 lbs. |
| Cell Count (visual) pores per inch | 50 ± 5/in. | 50 ± 5/in. |
| Retention of Tensile Strength after 5 hours steam Autoclave @ 120° C. | Min. 70% | Min. 70% |

Referring in particular to FIG. 2, the organizer 110 can also be provided with a double-sided adhesive strip 118 on a bottom surface of the base 112 of the organizer. The adhesive strip 118 allows the organizer 110 to be secured to a planar support surface 119, such as a tray or table top for example, to hold the organizer in place and further prevent surgical instruments supported thereon from toppling over and becoming disorganized. The adhesive strip 118 may further be provided in a sterile state.

Figure 4:
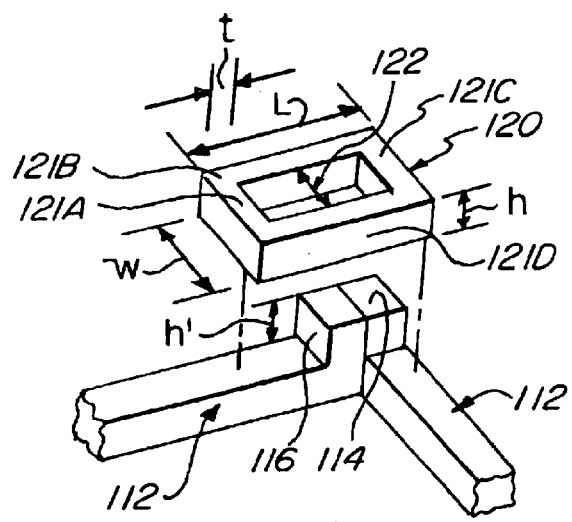
FIG. 4 is an exploded view, in perspective, illustrating a coupling device for coupling multiple instrument organizers in accordance with another embodiment of the present invention.

As illustrated in FIG. 4, multiple bases may be coupled together in order to increase the space available for supporting and organizing work pieces such as surgical instruments 200, 201, 202 (FIG. 3). In particular, during a given open-heart procedure a very large number of surgical instruments may be employed and those instruments may be used in a particular order. Accordingly, in order to provide additional space for instruments, eliminate the need for rolling up numerous towels and to ensure that, once placed in a particular order on multiple instrument organizers, the order of the instrument organizers will not change, a coupling device such as a collar 120 may be used to facilitate the connecting of multiple instrument organizers 110. More specifically, the collar 120 is disposed over and thereby connects end posts 114, 116 of adjacent bases 112. The bases 112 are preferably connected, as shown, with each longitudinal axis disposed perpendicular to the other, although, it will be understood that non-perpendicular angles are contemplated by the present invention. Optionally, the coupling device may be formed integrally with the bases 112, e.g., the end posts 114, 116 may each be configured to interlock with each other (not shown).

The collar 120, may be composed of the same material as the instrument organizer 110 discussed above and, may comprise a generally rectangular outer configuration. The collar 120 comprises a wall portion, in turn, comprising walls 121A, 121B, 121C, 121D and defining an aperture 122. The height (h) of the coupling device is preferably approximately equal to the height (h') of the posts 114, 116, e.g., to increase the area of contact and, in turn, the friction therebetween. The configuration of the aperture 122 is preferably generally rectangular in cross section and is preferably appropriately sized to receive the two end posts 114 and 116 with a frictional fit. While each of the end posts 114, 116 is illustrated as generally cubical in configuration, it will be understood that, any suitable configuration of the end posts and corresponding configuration of the aperture 122 may be employed.

A thickness (t) of each of the walls 121A, 121B, 121C and 121D may be approximately equal and each is preferably 0.5 inch for a coupling device that measures 3 inches in length (L) by 2 inches in width (W). However, it will be understood that thickness (t) may range from approximately 0.25 inch to approximately 0.75 inch.

Figure 5:
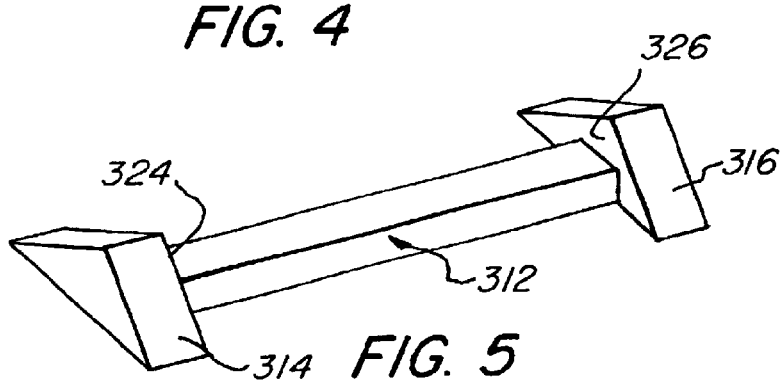
FIG. 5 is a perspective view of an instrument organizer having triangularly configured end posts in accordance with another embodiment of the present invention.

Referring to FIG. 5, a base, in accordance with another embodiment of the present invention, is illustrated generally at 312. In particular, the base 312 comprises a pair of end posts 314, 316 that are generally triangular in cross section. The end posts 314 and 316 may be formed integrally with the base 312, although, less preferably, may be formed separately then adhered to an opposing end of the base. The end posts 314, 316 comprise an engagement surface 324, 326, e.g., for supporting the surgical instruments 200, 201, 202 (FIG. 3). It will be recognized that the triangular outer configuration of the end posts enhances the stability of the base 312. It will also be recognized that a movable stabilizing post, such as that described above, may be used in conjunction with the present embodiment.

Figure 6:
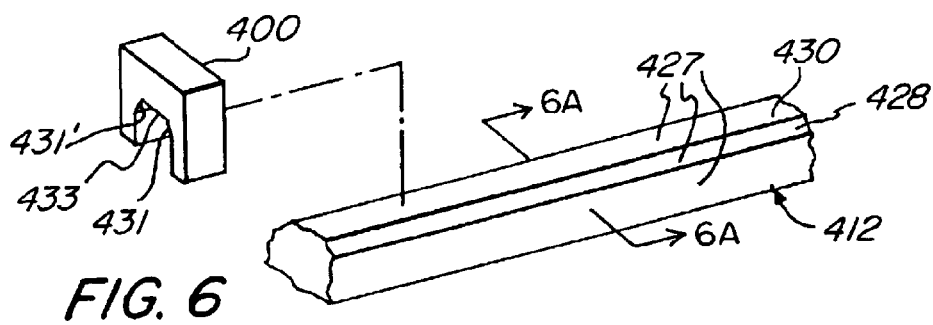
FIG. 6 is a perspective view of a portion of a base of an instrument organizer that has chamfered edges and of a movable stabilizing post in accordance with still another embodiment of the present invention.
Figure 6A:
FIG. 6A is a sectional view of the base taken along lines 6A of FIG. 6.
Figure 6B:
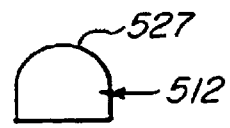
FIG. 6B is a view similar to that of FIG. 6A of a base of an instrument organizer that has a rounded surface in accordance with yet another embodiment of the present invention.

Referring now to FIGS. 6 and 6A, a portion of a base in accordance with still another embodiment of the present invention is shown generally at 412. The base 412 includes a contact portion 427 comprising a non-linear shape in cross section. In a particular embodiment, the contact portion comprises at least one chamfered surface 428, 428' and a top surface 430. Also, a movable stabilizing post 400 may be provided that comprises surfaces 431, 431' and 433 that may be correspondingly configured to engage the chamfered portions 428, 428' and the top surface 430. The chamfered portions 428, 428' assist in better stabilizing instruments 200, 201, 202 (see FIG. 3), when they are disposed on the base and increases friction with the movable stabilizing post 400 when it is mounted thereon. Optionally, in another embodiment, a base 512 includes a rounded contact portion 527 as shown in FIG. 6B. It will be understood that a movable stabilizing post 400 (FIG. 6), similar to that described above, may be correspondingly configured with a rounded portion to engage the base 512.

Figure 7:
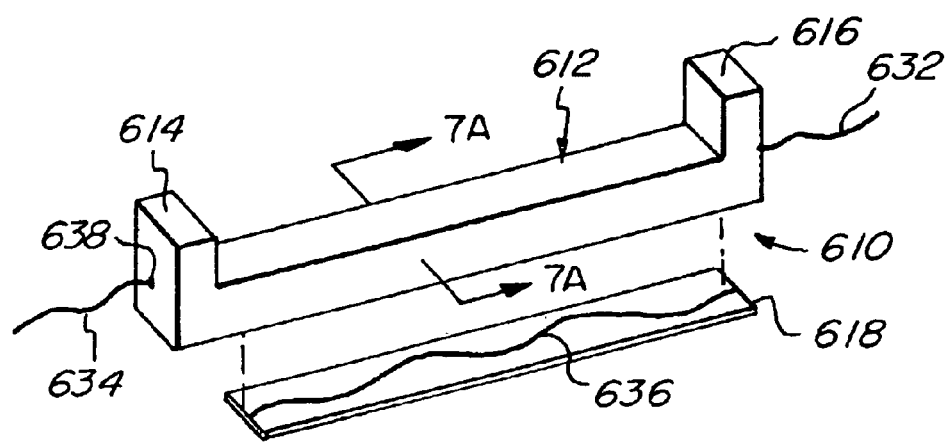
FIG. 7 is a perspective view of an instrument organizer optionally having radiopaque string mounted to a base in accordance with another embodiment of the present invention.

A further embodiment of an instrument organizer in accordance with the present invention is illustrated generally at 610 in FIG. 7. In this embodiment, the instrument organizer 610 comprises, or is composed of, a material that may be imaged by, for example, an X-ray machine. In particular, a radiopaque material such as a polymer or copolymer including a radiopaque substance embedded therein or, optionally, a metallic substance comprising platinum, gold or tungsten may be employed.

Another embodiment of the present invention is shown generally at 610 in FIG. 7. The instrument organizer 610 may be similar to that described above in connection with FIGS. 2 and 3, although, in the present embodiment the instrument organizer comprises a radiopaque material. In one particular embodiment, the radiopaque material comprises a radiopaque string 632, 634, 636 that is composed of a flexible polymer or copolymer with a radiopaque substance embedded therein. The radiopaque string 632, 634 may be inserted into a bore 638 in a post 614, 616 and then affixed by, e.g., an adhesive such as a silicone adhesive sold under the trademark RTV by the General Electric Company, Pittsfield, Mass. Also, the radiopaque string 636 may be located on an adhesive strip 618, which may be double sided, and which may be, in turn, adhered to the underside of the instrument organizer 610. Of course, rather than mounting the radiopaque strings to the instrument organizer, one or more of the radiopaque strings may be embedded within the base 612 and/or within a movable stabilizing post 100 (FIG. 2). Further in accordance with the present embodiment, the radiopaque strings 632, 634 or 636 may be used singularly or in any combination thereof. Also, radiopaque string 632, 634 or 636 may also be mounted to a movable stabilizing post 100 (FIG. 2) via an adhesive strip or a silicone adhesive as discussed above.

Suitable polymers for practice of this embodiment of the present invention include polyvinyl chloride and polyethylene. A suitable radiopaque substance is USP barium sulfate dispersed in the polymer in a sufficient quantity to render the polymer detectable by an operator on a x-ray image.

The radiopaque string may have a length which is in the range of approximately three inches to approximately 24 inches and may have a diameter that is within the range of between approximately 0.093 inch and approximately 0.125 inch, more preferably approximately 0.11 inch.

Figure 7A:
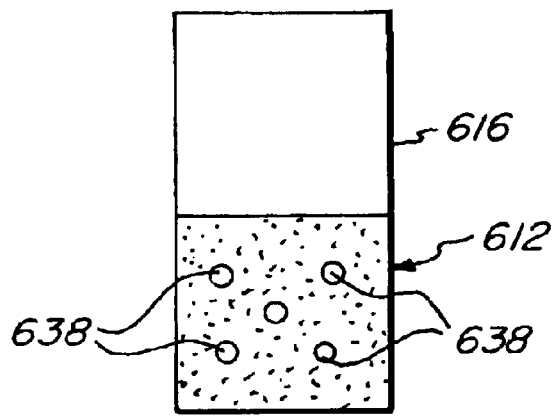
FIG. 7A is a sectional view of the base taken along lines 7A of FIG. 7 optionally having strands of radiopaque material embedded therewithin.

In a second optional embodiment, as illustrated in FIG. 7A, a plurality of strands 638 of radiopaque material may be embedded within the base 612 of the instrument organizer and/or embedded within a movable stabilizing post 100 (FIG. 2). The strands 638 may each be composed of a metallic substance such as platinum, gold or tungsten. A suitable diametrical size of the strands for imaging is within the range of approximately 0.0007 inch to approximately 0.0015 inch. Although not shown, it will be understood that, optionally, the strands 638 may be located, e.g., on the adhesive strip 618 rather than embedded within the base 612 and/or movable stabilizing post 100 (FIG. 2).

Figure 8:
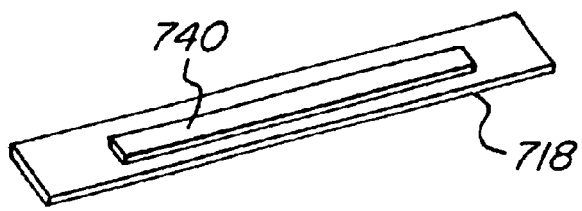
FIG. 8 is a perspective view of a radiopaque material mounted on an adhesive strip in accordance with another embodiment of the present invention.

In another optional embodiment illustrated in FIG. 8, a thin strip or layer 740 may be employed, for example, adjacent an adhesive strip 718. The layer 740 may be composed of an acetal homopolymer or nylon that is radiopaque. The adhesive strip 718 and layer 740 may be applied to a base structure (FIG. 7) and may be applied to a movable stabilizing post 100 (FIG. 2).

Figure 9:
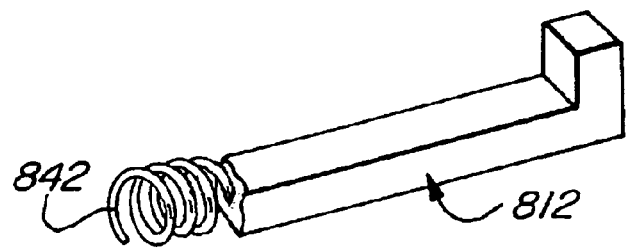
FIG. 9 is a perspective view of a base structure having a coil spring embedded therein in accordance with a further embodiment of the present invention.

A further optional embodiment is illustrated in FIG. 9. In particular, a metallic coil spring 842 may be embedded within a base 812 and may be embedded within a movable stabilizing post 100 (FIG. 2).

In a further optional embodiment and rather than utilizing radiopaque strings or strands as discussed above, radiopaque materials may be applied to, e.g., a base and a movable stabilizing post. Optionally, the radiopaque material may be affixed during the texturing or embossing steps of forming a base and a movable stabilizing post. This may be accomplished by using, as a carrying means, a piece or section of a suitable thermoplastic polymer which becomes slightly tacky or moldable at the temperatures of these steps and is compressed into the polyurethane foam of the base and/or movable stabilizing structure due to the pressure imparted by the rollers. Suitable materials comprise vinyl plastics and polyvinyl chloride containing X-ray grade barium sulfate dispersed therein.

Figure 10:
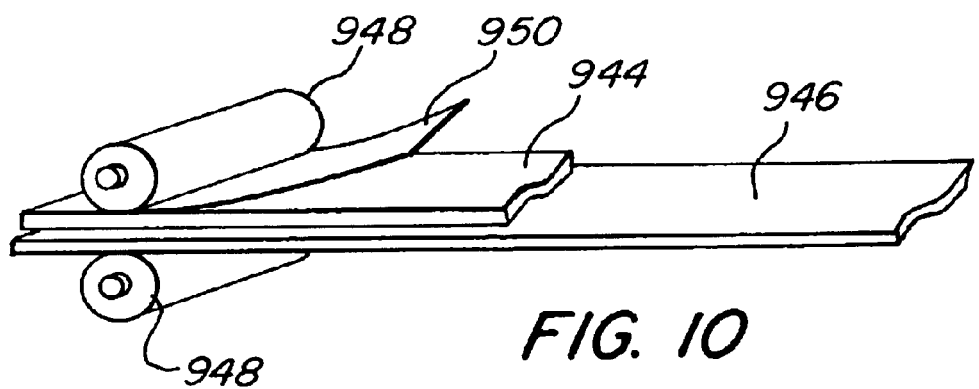
FIG. 10 is a schematic view of a blank disposed on a conveyer, a radiopaque material and roller for compressing the radiopaque material into the blank.

As shown schematically in FIG. 10, a blank 944 of polyurethane foam, having the properties described above in Table 1, may be conveyed by a conveyer 946 to a pair of rollers 948. The rollers 948 function to compress the radiopaque into the polyurethane foam blank 944 thereby causing the blank to be detectable on an X-ray image.

While the present invention has been described in connection with what is presently considered to be the most practical and preferred embodiments, it is to be understood that the present invention is not limited to the disclosed embodiments. Rather, it is intended to cover all of the various modifications and equivalent arrangements included within the spirit and scope of the appended claims.

What is claimed is:

1. A pair of instrument organizers comprising a couple for coupling the pair of instrument organizers together, each of the pair of instrument organizers comprising:

an elongated base structure having a top surface, a front surface and a rear surface, the front surface and the rear surface each extending from the top surface, and the front surface and the rear surface each disposed on opposing sides of the base structure, the elongated base structure comprising a width measured from the front surface to the rear surface and the elongated base structure including opposed terminal ends;

at least one upstanding post fixedly positioned at one of the terminal ends of the base structure; and at least one movable stabilizing structure comprising a body portion and self-gripping means extending away from the body portion and having portions of which engage the front and rear surfaces of the base structure for stabilizing and supporting at least one surgical instrument in a generally upright state at least partially on the organizer and the self-gripping means having a length that is not greater than a height of the base structure;

and the couple comprising a coupling device for connecting the pair of instrument organizers together.

2. The pair of instrument organizers of claim 1 wherein the elongated base structure of each instrument organizer is dimensioned and configured to support one end of the at least one surgical instrument, the elongated base structure of each instrument organizer also being dimensioned and configured to be mounted on a planar support surface which is able to support another end of the at least one surgical instrument.

3. The pair of instrument organizers of claim 1 wherein:

the body portion of each instrument organizer includes an upwardly extending post comprising a first side surface and a second side surface that each define a plane that extends in a direction that is generally perpendicular to a longitudinal axis of the elongated base structure when the movable stabilizing structure is mounted to the elongated base structure;

the self-gripping means of each instrument organizer having a pair of self-gripping legs that each include a first side surface and a second side surface each of which defines a plane that also extends in the direction that is generally perpendicular to the longitudinal axis of the elongated base structure when the movable stabilizing structure is mounted to the elongated base structure; and for each instrument organizer, the plane defined by the first side surface of the upwardly extending post and the planes defined by the first side surfaces of the self-gripping legs are generally coplanar and the plane defined by the second side surface of the upwardly extending post and the planes defined by the second side surfaces of the self-gripping legs are generally coplanar.

4. The pair of instrument organizers of claim 1 wherein the elongated base structure and the movable stabilizing structure of each instrument organizer comprises a lint-free foam plastic.

5. The pair of instrument organizers of claim 1 wherein the coupling device comprises a lint-free foam plastic.

6. The pair of instrument organizers of claim 1 wherein the coupling device comprises a wall portion defining an aperture that is dimensioned and configured to receive the upstanding posts of said instrument organizers when the upstanding posts are disposed in juxtaposition.

7. The pair of instrument organizers of claim 1 wherein the coupling device comprises a collar including a wall portion having a generally rectangular outer configuration and defining an aperture having a generally rectangular configuration for receiving the upstanding posts of the pair of instrument organizers and wherein each of the at least one upstanding posts has a cubical outer configuration.

8. A pair of instrument organizers for at least partially supporting surgical instruments, comprising a couple for coupling the pair of instrument organizers together, each of the pair of instrument organizers comprising:

an elongated base having a substantially uniform width and defining a continuous surface extending from a first side surface to an opposing second side surface thereof, the elongated base including two terminal ends;

at least one fixed end post extending from one of the terminal ends of the base; and at least one movable stabilizing structure including a central body having two self-gripping legs extending generally parallel to each other, the self-gripping legs having opposing, inwardly facing surfaces spaced apart a distance substantially equal to the width of the base, the opposing, inwardly facing surfaces of the two self-gripping legs being dimensioned and configured to solely grip the first and second side surfaces of the base, so that the movable stabilizing structure is attachable to the base and the central body is held in place by the self-gripping legs for retaining the surgical instruments in a generally upright state partially on the base, and the couple comprising a coupling device for connecting the pair of instrument organizers together, wherein for each instrument organizer, the central body of the movable stabilizing structure comprises an upwardly extending post comprising a first side surface and a second side surface that each define a plane that extends in a direction that is generally perpendicular to a longitudinal axis of the elongated base when the movable stabilizing structure is mounted to the elongated base;

each self-gripping leg of the movable stabilizing structure including a first side surface and a second side surface each of which defines a plane that also extends in the direction that is generally perpendicular to the longitudinal axis of the elongated base when the movable stabilizing structure is mounted to the elongated base; and the plane defined by the first side surface of the upwardly extending post and the planes defined by the first side surfaces of the self-gripping legs are generally coplanar and the plane defined by the second side surface of the upwardly extending post and the planes defined by the second side surfaces of the self-gripping legs are generally coplanar.

9. The pair of instrument organizers of claim 8 wherein the coupling device comprises a wall portion defining an aperture that is dimensioned and configured to receive said end posts when the end posts are disposed in juxtaposition.

10. The pair of instrument organizers of claim 8 wherein the coupling device comprises a collar including a wall portion having a generally rectangular outer configuration and defining an aperture having a generally rectangular configuration for receiving the end posts and wherein each end post has a cubical outer configuration.

11. The pair of instrument organizers of claim 8 wherein the elongated base and the movable stabilizing structure of each instrument organizer comprises a lint-free foam plastic.

12. The pair of instrument organizers of claim 8 wherein the coupling device comprises a lint-free foam plastic.

13. The pair of instrument organizers of claim 8 wherein for each organizer, a height of the elongated base is greater than a length of each of the self-gripping legs such that a bottom surface of the central body will grip the continuous surface of the elongated base.

14. The pair of instrument organizers of claim 8 wherein for each organizer, a height of the elongated base is approximately equal to a length of each of the self-gripping legs such that a bottom surface of the central body will grip the continuous surface of the elongated base.

15. The pair of instrument organizers of claim 8 further comprising double sided self adhesive strips each attached to a bottom surface of the elongated base of each of the instrument organizers.

* * * * *